(12) United States Patent
Petrek

(10) Patent No.: US 8,524,170 B2
(45) Date of Patent: Sep. 3, 2013

(54) PIPETTE AND SEALING TIP

(75) Inventor: James S. Petrek, Danville, CA (US)

(73) Assignee: Rainin Instrument, LLC, Oakland, CA (US)

(*) Notice: Subject to any disclaimer, the term of this patent is extended or adjusted under 35 U.S.C. 154(b) by 0 days.

(21) Appl. No.: 13/032,612

(22) Filed: Feb. 22, 2011

(65) Prior Publication Data

US 2012/0213677 A1     Aug. 23, 2012

(51) Int. Cl.
*B01L 3/02* (2006.01)
(52) U.S. Cl.
USPC ........... 422/525; 422/500; 422/501; 422/504; 422/511; 422/524; 422/931; 422/932; 73/863.32; 73/864; 73/864.01; 73/864.13; 73/864.14; 73/864.16

(58) Field of Classification Search
USPC ............... 422/500–501, 504, 511, 524, 525, 422/931–932; 73/863.32, 864, 864.01, 864.13, 73/864.14, 864.16
See application file for complete search history.

(56) References Cited

U.S. PATENT DOCUMENTS

| | | | |
|---|---|---|---|
| 3,757,585 A * | 9/1973 | Heller et al. ............... 73/864.18 |
| 4,023,716 A | 5/1977 | Shapiro |
| 4,046,291 A * | 9/1977 | Goda ............................ 222/309 |
| 4,151,750 A * | 5/1979 | Suovaniemi et al. ....... 73/864.14 |
| 4,237,094 A * | 12/1980 | Suovaniemi et al. ....... 73/864.17 |
| 4,283,950 A * | 8/1981 | Tervamaki ................. 73/864.14 |
| 4,464,941 A | 8/1984 | Herold et al. |
| 4,474,071 A | 10/1984 | Marteau d'Autry |
| RE32,210 E * | 7/1986 | d'Autry ..................... 73/864.14 |
| 4,672,857 A | 6/1987 | MacDermott |
| 4,679,446 A * | 7/1987 | Sheehan et al. ............. 73/864.13 |
| 4,748,859 A * | 6/1988 | Magnussen et al. ........ 73/864.01 |
| 4,824,641 A * | 4/1989 | Williams .......................... 422/64 |
| 4,830,832 A * | 5/1989 | Arpagaus et al. .............. 422/65 |
| 4,863,695 A * | 9/1989 | Fullemann .................... 422/501 |
| 4,933,291 A * | 6/1990 | Daiss et al. .................... 436/45 |
| 5,104,624 A * | 4/1992 | Labriola ....................... 422/516 |
| 5,200,151 A * | 4/1993 | Long ............................. 422/511 |
| 5,218,875 A * | 6/1993 | Volpe et al. ................. 73/864.01 |
| 5,223,226 A * | 6/1993 | Wittmer et al. ............... 422/508 |
| 5,232,669 A * | 8/1993 | Pardinas ....................... 422/526 |
| 5,435,197 A * | 7/1995 | Telimaa et al. ............. 73/864.14 |
| 5,614,153 A * | 3/1997 | Homberg ..................... 422/525 |
| 5,700,959 A | 12/1997 | Homberg |
| 5,770,160 A * | 6/1998 | Smith et al. .................. 422/525 |
| 6,045,757 A | 4/2000 | Moriarty |
| 6,117,394 A * | 9/2000 | Smith ........................... 422/513 |
| 6,168,761 B1 | 1/2001 | Kelly |
| 6,482,361 B1 * | 11/2002 | Suovaniemi ................. 422/525 |
| 6,499,364 B1 * | 12/2002 | Suovaniemi ............... 73/864.15 |
| 6,702,990 B1 * | 3/2004 | Camacho et al. ............. 422/513 |
| 6,780,381 B2 | 8/2004 | Yiu |
| 6,787,367 B1 * | 9/2004 | Suovaniemi et al. ......... 436/180 |
| 7,033,543 B1 * | 4/2006 | Panzer et al. ................. 422/525 |
| 7,318,911 B2 * | 1/2008 | Smith ........................... 422/513 |
| 7,335,337 B1 * | 2/2008 | Smith ........................... 422/513 |
| 7,595,027 B2 * | 9/2009 | Itoh .............................. 422/523 |
| 7,641,859 B2 * | 1/2010 | Cote et al. .................... 422/522 |
| 7,662,343 B2 | 2/2010 | Mathus |

(Continued)

*Primary Examiner* — Brian R Gordon
(74) *Attorney, Agent, or Firm* — Clarke A. Wixon

(57) ABSTRACT

A sealing pipette tip includes features to seal the tip directly against the piston in an air displacement pipette, avoiding the need for a piston seal within the pipette. This configuration reduces potential points of failure, allows the pipette-tip interface to be optimized, and improves liquid handling characteristics of the pipette.

9 Claims, 12 Drawing Sheets

(56) References Cited

U.S. PATENT DOCUMENTS

| | | | |
|---|---|---|---|
| 7,662,344 B2* | 2/2010 | Mathus et al. | 422/513 |
| 7,785,466 B1* | 8/2010 | Smith | 210/321.75 |
| 8,071,050 B2* | 12/2011 | Smith | 422/501 |
| 2003/0039589 A1* | 2/2003 | Smith | 422/100 |
| 2004/0071602 A1* | 4/2004 | Yiu | 422/100 |
| 2008/0078258 A1 | 4/2008 | Price | |
| 2009/0280033 A1* | 11/2009 | Cote et al. | 422/100 |
| 2010/0034706 A1* | 2/2010 | Mathus et al. | 422/100 |
| 2010/0196210 A1* | 8/2010 | Jungheim et al. | 422/100 |
| 2011/0174087 A1 | 7/2011 | Kimura | |

* cited by examiner

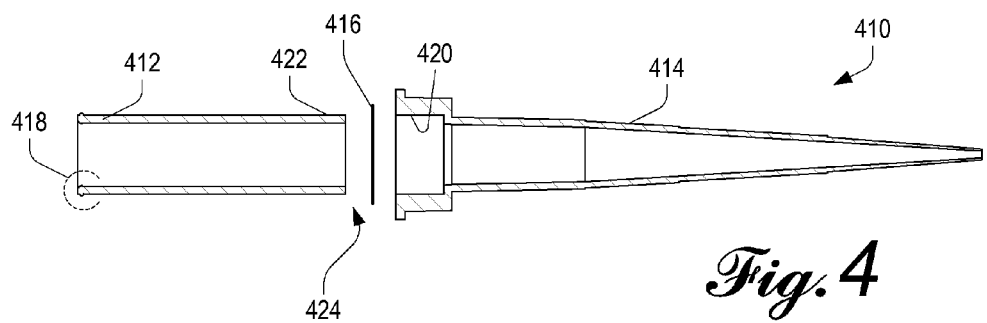
Fig. 4
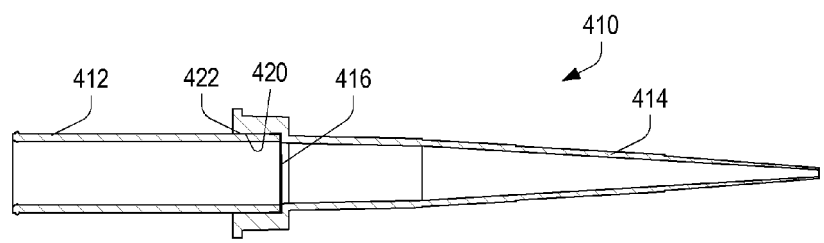
Fig. 5
Fig. 6
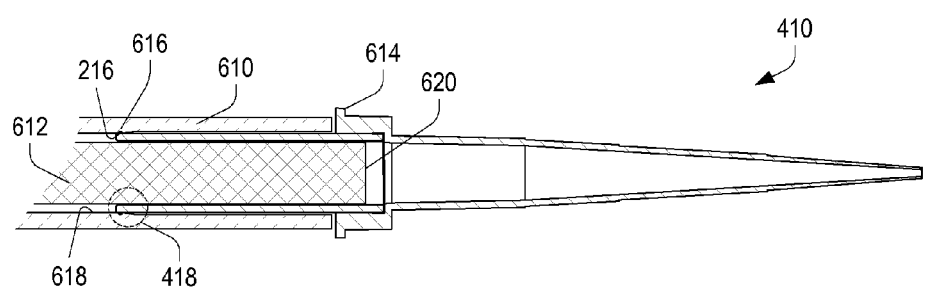

PIPETTE AND SEALING TIP

FIELD OF THE INVENTION

The invention relates to air displacement pipettes and sealing disposable tips for such pipettes, and particularly to air displacement pipettes without piston seals, where piston sealing is accomplished via a structure integral to the sealing disposable tip.

BACKGROUND OF THE INVENTION

Handheld pipettes are commonly used to dispense or transfer small but accurately measured quantities of liquids.

Air displacement pipettes are the most common variety of handheld pipettes. In an air displacement pipette, a controllable piston is mounted for movement axially within a chamber in the pipette; the piston moves in response to either manual or motorized electronic control. Typically, the piston moves in a chamber in the liquid end, or shaft, of the pipette, to which disposable pipette tips may be mounted.

An air tight seal is formed between the piston and the shaft. With such a seal in place, axial movement of the piston will vary the size of the airspace within the shaft. Moving the piston downward, into the shaft, will reduce the airspace and force air out of the shaft through an open distal end. Moving the piston upward, out of the shaft, will increase the airspace and cause air to be drawn into the shaft through the open end. The seal between the piston and the shaft is generally formed with a compressed O-ring or a similar structure, fabricated from a material that provides satisfactory long-term performance. For example, a piston seal structure may be made from polyethylene combined with PTFE, which has been found to offer good sealing performance and wear resistance and reliability over a period of months, although such seals do tend to break down and leak over the course of time. Other configurations are possible, including various dry or lubricated seals.

A disposable pipette tip is then sealed to the open distal end of the shaft. Then, as the piston is moved within the shaft, air—or a measured quantity of liquid equal in volume to the displaced air—is drawn into or forced out of the tip. With both the piston and the tip sealed to the shaft, the only entry and exit path should be the distal open end of the disposable pipette tip. Because of the sealed system, air displacement pipette may be used to make accurate and precise measurements, and to move carefully calibrated quantities of liquids.

In general, disposable tips attach to the shaft of a pipette through a simple friction fit. The two most common and commercially successful pipette tip fitting standards are the standard conical mount and the LTS® system offered by Rainin Instrument, LLC. In both cases, the friction fit between the shaft and the disposable tip also enables an air-tight seal. One version of the LTS pipette tip is described in U.S. Pat. No. 6,168,761, which is hereby incorporated by reference as though set forth in full. The LTS tip, as shown, seals against the pipette shaft along a single, thin, annular sealing band, and the commercial success of the LTS system shows that successful and repeatable sealing, with low friction, may be accomplished with such a configuration.

Other tip mounts have been attempted but have not met with great commercial success. Matrix Technologies Corporation offers a tip with tabs that lock into corresponding features in the pipette shaft. See U.S. Pat. No. 7,641,859 to Cote et al. Viaflo Corporation has a solution that includes a lobed shaft that locks into corresponding features within the tip. See U.S. Pat. No. 7,662,343 to Mathus et al. Sorenson BioScience sells a dual-material pipette tip for traditional pipette shafts that employs a second material to optimize the mount, but still seal adequately. These dual-material tips have a rigid polypropylene distal end for handling liquids, and a soft thermoplastic elastomeric mount portion overmolded thereon. See U.S. Patent Application Publication No. 2008/0078258 to Price et al. Tips for robotic applications from Apricot Designs have external seal rings that seal to the inner barrel of a tip holder. See U.S. Pat. No. 6,780,381.

All of these alternative pipette tips share a common attribute: not only do they require a seal between the tip and the shaft, but they also require a seal between the shaft and the piston. There are two seals, and two potential points of failure. The seal between the tip and the shaft is replaced every time a tip is discarded and replaced with a new one, but the seal in the pipette is serviced infrequently. This may lead to leaks and other failures, which in turn may lead to inaccuracy in liquid measurement or failure in pipetting operations.

In general, seal failure (such as wear, splitting, other damage, misalignment, dislodgment, corrosion, or contamination) is a common cause of pipetting failure. These failures can lead to failed outcomes, and may be difficult to identify in advance, or even as pipetting is ongoing. Wear and damage to the shaft in the tip mount region can also result in failures, and for this reason, plastic pipette shafts are also replaced from time to time.

These problems may be mitigated to some extent by performing frequent calibrations and having pipette serviced relatively often. Best practices in this regard frequently involve regular seal replacement, even if it does not appear necessary. Such maintenance often involves fairly significant teardown of the pipette, which requires dedicated labor and calibration upon reassembly. It has the potential to take a pipette out of service for a period of time.

Another consequence of the traditional pipette configuration—with the piston moving within a cavity in the shaft, which is in turn connected to a disposable tip—is the existence of significant empty ullage space over the liquid. A substantial cushion of air exists between the piston and the liquid level in the tip. This cushion of air is capable of expansion and contraction when acted upon, serving as a flexible "spring" between the position of the piston and the liquid level. This additional movement is undesirable, and may lead to volume inaccuracies. Moreover, the cushion of air is potentially subject to liquid evaporation into the air, heating, and cooling, and resulting expansion and contraction effects, which may further affect the accuracy of pipetting operations. High accuracy is still possible, but it is largely dependent on appropriate technique being employed by the user.

In traditional pipette tips, protection from cross-contamination is generally accomplished by inserting a disc or cylinder of porous filter media near the proximal end, between the mount of the pipette tip and the liquid-handling portion. The filter allows air to pass through, but inhibits aerosols and liquids. Such filtered tips must be larger than unfiltered tips for the same liquid volume capacity (because of the space occupied by the filter, plus a gap between the filter and the liquid level). Filters also tend to impede airflow, and are relatively inefficient and expensive to produce and insert into pipette tips. Because of this, filtered pipette tips are generally more expensive than their unfiltered counterparts.

SUMMARY OF THE INVENTION

Accordingly, a handheld pipette according to the invention addresses some of the shortcomings of presently commercially available handheld pipettes, as described above, and enables additional features not generally available using traditional pipettes.

An embodiment of the pipette disclosed herein includes a shaft with mounting features specially adapted for the tips described herein. The pipette includes a piston that seals against a proximal end of the tip, and no portion of the pipette itself.

Accordingly, a new seal is made every time a disposable pipette tip according to the invention is replaced. Because there is no seal between the piston and the pipette shaft, there is a reduced need for regular pipette maintenance and calibration. There is no seal to wear, break, or replace.

Similarly, because a tip according to the invention only forms an air-tight seal against the piston (which is generally metal, but may be some other material highly resistant to wear, such as glass, ceramic, or plastic), an externally damaged pipette shaft will not breach the tip's integrity, causing a leak.

A pipette and tip according to the invention may benefit from low insertion and ejection forces, with a positive "snap" into place as the shaft and tip interlock as described with reference to an embodiment illustrated herein. The low insertion and ejection forces are particularly advantageous with respect to traditional, conical pipette tips and pipettes with corresponding shaft designs.

A pipette and tip as described herein may have reduced ullage space, because the piston directly penetrates and seals against the tip. This may makes the pipette easier to use, and reduce the effect of user technique on pipetting accuracy.

A two-piece tip configuration is described herein, which enables the optional use of an efficient low pore size membrane filter, some advantages of which are described in U.S. Pat. No. 6,045,757 to Moriarty et al. With two pieces, one for the mount end of the tip and one for the liquid handling end of the tip, two different materials may be used. Different colors may be employed. A mount material may be selected to optimize the stability of the tip on the shaft, insertion/ejection characteristics, and the mechanical interface between the tip and the shaft, since it is not necessary to maintain an air tight seal between the shaft and the tip, and the mount portion of the tip generally remains free from liquid contact. Also advantageously, the liquid handling material may be made as pure and chemical resistant as possible, without affecting mounting characteristics.

Accordingly, then, an embodiment of a sealing pipette tip according to the invention has a generally elongated tubular configuration with an open proximal end and a narrow open distal end, in a form factor in some ways comparable to traditional pipette tips. In one embodiment disclosed herein, the open proximal end of the pipette tip has an inward-facing sealing region, which in the disclosed embodiment comprises a projecting ring.

An exemplary pipette according to the invention for use with such tips includes a piston that moves axially into the tip, past the seal, while interlocking features on the tip and the shaft of the pipette hold the tip in place. There is no need for a piston seal within the pipette.

When the pipette tip is mounted on the pipette, the open proximal end of the pipette tip receives the piston, and the sealing ring forms an air tight seal around the piston. In an embodiment of the invention, a controlled amount of physical interference between an internal surface of the shaft and the proximal open end of the tip causes the open end to constrict and seal around the piston when the tip is mounted.

Because the seal is made between the stationary sealing ring and the moving piston, as the piston moves through the seal during operation of the pipette, the precisely manufactured and consistent surface of the piston displaces a consistent and predictable quantity of air, ensuring that the performance of a pipette according to the invention remains consistent and accurate, regardless of minor variations in the shape or configuration of the pipette tip. This is in contrast to positive displacement pipettes (such as illustrated in U.S. Pat. No. 4,023,716 to Shapiro), where the edge of a piston forms a moving seal against a cylindrical interior of a pipette tip, and where tip shape inconsistencies (such as variations in the inner tip diameter) can lead to poor performance and volume inaccuracies.

Accordingly, a number of shortcomings of other known pipettes and tips are remedied by pipettes and tips according to the invention.

BRIEF DESCRIPTION OF THE DRAWINGS

These and other objects, features, and advantages of the invention will become apparent from the detailed description below and the accompanying drawings, in which:

FIG. 4 is an exploded sectional view of the parts present in the pipette tip illustrated in FIG. 2;

FIG. 5 is a sectional view of the pipette tip illustrated in FIG. 2, demonstrating the fit among the parts shown in FIG. 4;

FIG. 6 is a sectional view of the tip illustrated in FIG. 2, showing the pipette tip mounted on a pipette shaft and sealing against a piston;

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
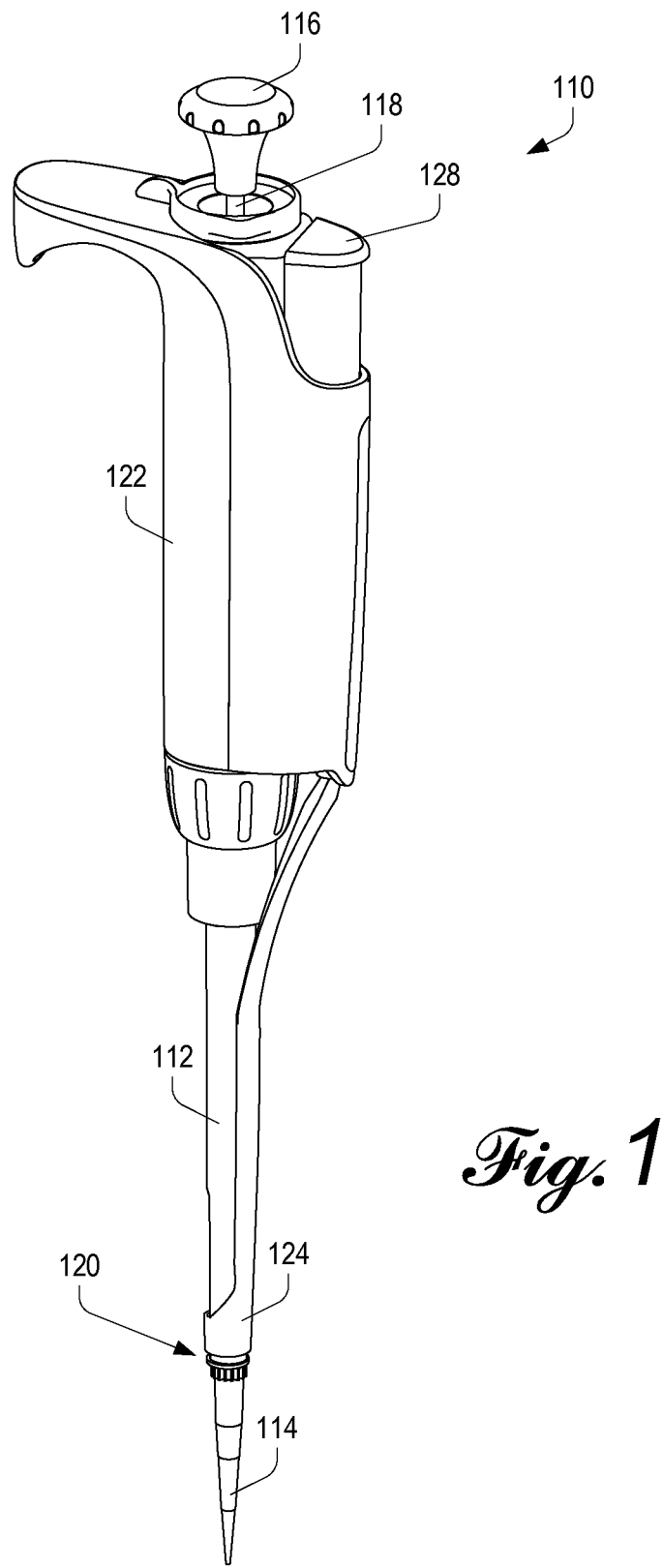
FIG. 1 represents a handheld pipette according to the invention with a sealing pipette tip according to the invention mounted thereon.

Referring initially to FIG. 1, a handheld pipette 110 according to the invention is shown. As with traditional pipettes, the illustrated pipette 110 has a tip-mounting shaft 112, and a sealing tip 114 according to the invention is shown mounted on the shaft 112.

The overall form factor of the pipette 110 and the sealing tip 114 is comparable to that of traditional pipettes, and the combination is used in the same ways and using the same techniques as would be performed using traditional pipettes.

The pipette has a plunger button 116 connected to a plunger rod 118. The button 116 and rod 118 are spring-biased to a fully-extended position. The plunger rod 118 is coupled to a piston within the pipette 110 (not shown). And as with traditional pipettes, when the plunger button 116 is depressed, it moves the plunger rod 118 and the piston downward through the shaft 112 toward a distal end 120 of the shaft 112, from its uppermost position against an upper stop.

As in traditional manual pipettes, the plunger button 116 is spring-biased relative to two positions, namely a released and extended position and a home position. There is a fully-depressed blowout position when the plunger button 116 is depressed past the home position. With no pressure applied to the plunger button 116, a plunger spring biases the plunger button 116 upward against an upper volume-setting stop, the position of which is adjusted by turning the plunger button 116 and a stop position adjustment mechanism as discussed above. In this position, the plunger rod 118 and plunger button 116 are at the released and extended position with respect to the body 122 of the pipette 110.

At the home position, with the plunger button 116 partially depressed, the resistance to depression of the plunger button increases. As is common in handheld pipette construction, a secondary blowout spring adds to the resistance offered by the plunger spring. The increased resistance is sensed by the pipette user and defines the home position. Between the released and extended position and the home position, only the plunger spring biases the plunger button position upward toward its extended position, and a relatively light first force level is required to act against the spring bias.

The plunger button 116 is released from the home position to the fully extended position to aspirate a desired volume of liquid, and subsequently moved from the extended position to the home position to dispense the liquid.

Between the home position and a fully-depressed blowout position, both the plunger spring and the blowout spring act upward against the plunger button 116, and a higher second force level is required to act against the spring bias. This configuration including a primary plunger spring and a secondary blowout spring is common in handheld pipettes.

After dispensing, the plunger button 116 is moved from the home position through to the end of the blowout position to eject any remaining liquid from the pipette tip 114.

Accordingly, at the home position, the user feels a tactile transition between the two spring forces, and by exerting a force between the first level and the higher second level, the user can easily keep the plunger button 116 at the home position.

In a traditional handheld pipette, the plunger button acts directly through the plunger rod to a piston, which maintains an air-tight seal with the liquid end of the pipette via a seal within the pipette. The seal remains in a fixed position with respect to the liquid end and further forms an air-tight seal with respect to an interior portion of the liquid end. Accordingly, as the plunger button is manipulated, the piston is caused to move through the seal and displace an air volume within the liquid end. As an orifice is provided at a distal end of the pipette tip, and a substantially air-tight seal is maintained at all other places, the only path for a liquid (or any fluid) to enter or exit the tip is via the orifice, and there is a deterministic relationship between the volume of air displaced by the piston and the volume of liquid manipulated by the pipette.

In a pipette according to the invention, there is no seal within the pipette itself. Rather, in the disclosed embodiment (illustrated in FIGS. 2-13, below) the pipette tip 114 includes a sealing region in the form of an inwardly projecting ring, and the piston is caused to move axially within the tip 114. Accordingly, an air-tight seal is formed at the proximal end of the tip 114, and air volume only within the tip is displaced to move liquid in and out of the pipette tip 114.

In many regards, and as illustrated in detail in FIG. 22 (and discussed below), the pipette 110 may be configured similarly to a traditional handheld manual or electronic pipette. The same volume setting mechanisms, springs, drive mechanisms, plunger mechanisms, and body parts may generally be employed. The primary differences reasonably necessary for a pipette 110 according to the invention to function as described herein are: the shaft on the liquid end of the pipette should be adapted to accommodate a tip according to the invention as described below; no seal (or any other related structure) is necessary between the air displacement piston of the pipette and any portion of the pipette 110; the piston may be longer and otherwise adjusted in diameter and travel so that the piston moves within a space in the tip 114 as described below; and the tip ejector 124 may need to be reconfigured to fit the new shaft and tip.

One exemplary pipette configuration that may be employed and reconfigured as set forth herein is described in U.S. Pat. No. 5,700,959 to Homberg, which is hereby incorporated by reference as though set forth in full.

Figure 2:
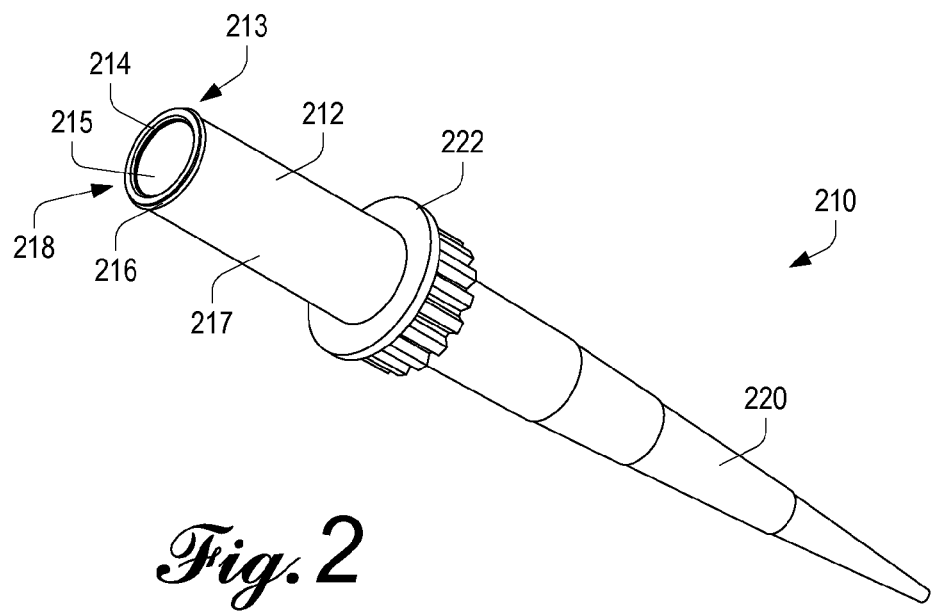
FIG. 2 illustrates an exemplary pipette tip according to the invention that accommodates approximately 200 μl of liquid, and emphasizes the proximal mount end of the pipette tip.

One embodiment of a pipette tip according to the invention is illustrated in FIG. 2. The illustrated pipette tip 210 accommodates a liquid volume of approximately 200 μl in this configuration. A mount portion 212 of the pipette tip 210 extends into the shaft 112 of the pipette 110 and seals against the piston near its proximal end 213; the mount portion 212 will be described in further detail below in connection with FIGS. 4-6. As shown in FIG. 2, the mount portion 212 includes an annular sealing ring 214 around an interior surface 215 at the proximal end 213, and an annular mount projection 216 around an exterior surface 217 also at the proximal end 213. An open end 218 of the mount portion 212 receives the piston as described above and in further detail below.

Between the mount portion 212 and a liquid handling portion 220 of the pipette tip 210 is a peripheral shelf 222 that extends radially outward from the pipette tip. This peripheral shelf 222 may serve as a stop for the distal end 120 of the pipette shaft 112 when the pipette tip 210 is mounted to the pipette 110, and provides a surface for a pipette-mounted tip ejector 124 (FIG. 1) to act against. It may also be useful to stabilize the pipette tip 210 against lateral forces exerted against the liquid handling portion 220 of the pipette tip 210 during usage. It will be noted that for insertion limiting and stabilization purposes, the peripheral shelf 222 tends to act in cooperation with the mount projection 216 (and corresponding recess in the shaft 112). In an alternative embodiment of the invention, the shelf 222 is not used to limit insertion depth; an internal step within the shaft 112 serves that purpose. In any case, when the tip 210 is mounted properly to the pipette and the mount projection 216 is engaged with a corresponding recess in the shaft 112 (as discussed below in connection with FIG. 6), the shelf 222 preferably is close to but not in contact with the distal end 120 of the shaft 112.

Figure 3:
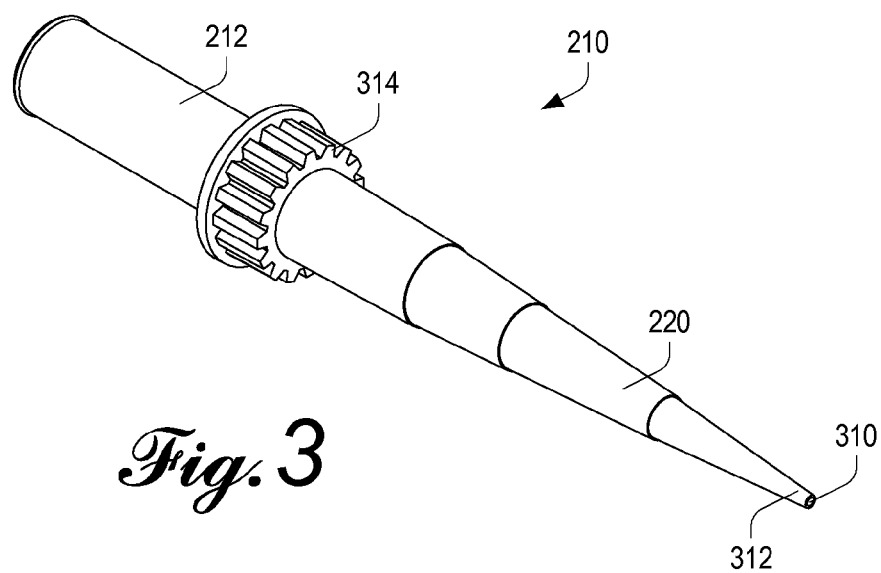
FIG. 3 presents an alternative view of the pipette tip of FIG. 2, emphasizing the distal liquid-handling end of the pipette tip.

Another view of the pipette tip 210 of FIG. 2 is presented in FIG. 3, illustrating an orifice 310 at a distal end 312 of the pipette tip 210. A plurality of radial fins 314 are arranged around an exterior of the pipette tip 210; these fins 314 provide a relatively wide surface to rest against an upper surface in a pipette rack, stiffen the pipette tip 210 against lateral bending, and further provide texture for ease in gripping and maneuvering pipette tips by hand. There may also be an aesthetic or trade-dress component to the configuration of the fins 314 on the pipette tip 210. In the disclosed embodiment, the fins 314 are adjacent to and below the peripheral shelf 222 on the pipette tip 210, though other configurations are possible.

FIGS. 4, 5, and 6 illustrate a sealing pipette tip according to the invention in cutaway form, viewed along a plane extending along the longitudinal axis of the tip 210 (FIG. 2).

One embodiment of a sealing pipette tip 410 according to the invention includes three constituent parts, and is illustrated in an exploded view in FIG. 4.

The pipette tip 410 of FIG. 4 includes a proximal mount segment 412, a tapered distal liquid handling segment 414, and a membrane filter 416. The parts are pressed together to form an interference fit, preferably without adhesive, and an air-tight seal is maintained between the proximal mount segment 412 and the distal liquid handling segment 414.

A connection end 418 of the proximal mount segment 412 attaches to a pipette according to the invention; the connection end 418 will be illustrated in greater detail and described below with reference to FIG. 12.

The disclosed membrane filter 416 is a polymer, such as expanded PTFE or a woven or fibrous material. Such material is generally hydrophobic, but permits relatively free passage of dry air. Using such a material as a pipette tip filter will effectively prevent liquids from reaching the pipette shaft and piston, even when in very small droplets. The membrane filter 416 is an optional component of a sealing tip 410 according to the invention, and if protection of the pipette's piston is not necessary or advantageous, it may be omitted. Alternative forms of filters, such as porous plastic plugs, may also be employed in a tip according to the invention.

The disclosed sealing pipette tip 410, being assembled from separate components, may advantageously employ separate materials for the mount segment 412 and the liquid handling segment 414.

Traditional pipette tips are generally molded from virgin polypropylene, without a substantial quantity of additives (although some pipette tips may include small quantities of coloring agents). A sealing pipette tip 410 according to the invention may also be assembled from components of injection-molded polypropylene, but certain advantages may be realized to altering the composition of either the mount segment 412, the liquid handling segment 414, or both.

For example, the mount segment 412 may be molded from either polypropylene or another polymer, impregnated with a desired proportion of a lubricity-enhancing agent like PTFE (polytetrafluoroethylene, commonly known as DuPont TEFLON®). The composition of the mount segment 412 may thus be adjusted to provide a firm mount to the pipette shaft 112 (FIG. 1) while maintaining smooth and leak-free seal to the piston (as shown in FIG. 6 and described in further detail below). Alternatively, a thermoplastic elastomer that is softer than polypropylene or polyethylene may be used for the mount segment 412, thereby reducing the force required to mount or eject the sealing tip 410 from the pipette 110, and similarly reducing drag on the piston.

Moreover, the use of two separate segments in the tip 410 permits various additives to be used in the mount segment 412, which may or may not be chemical resistant, without compromising the performance of the sealing tip 410 or the purity of any liquids contacted by the liquid handling segment 414. Accordingly, the mount segment 412 may be colored more aggressively, or made of various physically desirable materials, that would otherwise be considered unacceptable in a traditional pipette tip.

Similarly, the liquid handling segment 414 may contain a low-retention additive or coating, to discourage adhesion of certain liquids to the tip, without adversely impacting the mount between the sealing tip 410 and the pipette.

Although the tip 410 is described above as being assembled from separate molded components, it should be recognized that a tip using multiple materials (but generally without a membrane filter) may be manufactured using an overmolding technique. Under some circumstances it may be more advantageous or cost-effective to do so.

FIG. 5 shows the sealing pipette tip 410 according to the invention in assembled form. As shown in FIG. 5, a relatively tight friction fit between an interior surface 420 (FIG. 4) of the liquid handling segment 414 and an exterior surface 422 (FIG. 4) of the mount segment 412 is sufficient to hold the parts together in an air-tight assembly, and to maintain a desired position of the membrane filter 416 between the mount segment 412 and the liquid handling segment 414. As disclosed, the membrane filter 416 is sized slightly larger than the outer diameter of a cylindrical end 424 (FIG. 4) of the mount segment 412, and when the parts are pressed together, the membrane filter 416 bends around the flat cylindrical end 424 of the mount segment 412 and is held securely in place within the liquid handling segment 414.

The optional membrane seal 416 separates the mount segment 412 from the liquid handling segment 414, allowing air to pass relatively freely between the two segments while impeding the flow of liquids, aerosol droplets, and particulates. The junction between the liquid handling segment 414 and the mount segment 412 is air-tight and fluid-tight, and as shown in FIG. 5 depends on an interference fit to maintain the fit and seal between the two segments. It will be appreciated that other connection means, such as a ring-and-groove joint, may also be employed to similar effect. The membrane seal 416 may also be welded to either the mount segment 412 or the liquid handling segment 414 prior to the two segments being joined, or all components may be welded, bonded, or otherwise affixed together using an adhesive.

FIG. 6 shows the assembled sealing pipette tip 410 of FIG. 5 mounted on a portion of pipette shaft 610, and further illustrating a pipette piston 612 within the sealing tip 410.

As illustrated, a peripheral shelf 614 abuts (or is close to) a distal end of the pipette shaft 610, the mount segment 412 of the sealing tip extends into an interior of the pipette shaft 610. The piston 612 extends within the mount end 412 of the sealing tip 410.

The sealing tip 410 couples to the shaft 610 by way of the mount projection 216 (FIG. 2), which engages a corresponding and mating mount recess 616 extending around an interior surface 618 of the shaft 610. This engagement causes the sealing tip 410 to remain securely mounted on the pipette shaft 610, even as the piston 612 slides longitudinally within the sealing tip 410, contacting and sealing against the sealing ring 214 (FIG. 2). The interaction of the mount projection 216, the sealing ring 214 (FIG. 2), and other portions of the connection end 418 of the mount segment 412 with the shaft 610 and the piston 612 will be illustrated in further detail below in connection with FIG. 13.

With the pipette 110 set to its maximum volume setting, when the piston 612 is in the released and extended position (and little or no pressure is exerted on the plunger button 116), a distal face 620 of the piston 612 only slightly penetrates the mount segment 412 of the pipette tip 410, a distance sufficient for the piston 612 to engage the sealing ring 214 and form an air-tight seal, and preferably little further. As the plunger button 116 is depressed, the piston 612 moves into the mount segment 412, displacing air within the pipette tip 410. And at the lowest point of the plunger button 116 corresponding to a completed blowout stroke, the distal face 620 of the piston 612 may be almost directly adjacent to the membrane filter 416, as illustrated in FIG. 6. Accordingly, the size of the space within the mount segment 412 of the pipette tip 410 must be at least the maximum liquid volume of the pipette tip 410 plus enough additional volume for the blowout stroke, and is preferably minimally larger than that.

This minimization of air volume tends to improve pipetting performance. Better accuracy and precision can be maintained in low volume ranges (particularly in 2 µl and 10 µl pipettes, and similar volume ranges with their corresponding tips, an embodiment of which is illustrated in FIGS. 7-11). The blowout stroke tends to be more effective (as blowout displaces more of the total air volume than is possible using a traditional pipette configuration). Accuracy and precision may be improved even in larger volume pipettes, when used in the lower portion of their adjustable volume ranges.

It should be noted that although the embodiment of the sealing tip 410 illustrated in FIGS. 4-6 is assembled from several parts, an alternative form may be manufactured as a single part, by injection molding or another suitable technique. Where the tip itself is fabricated in this manner, a traditional porous plastic filter may be inserted, as in commercially available traditional pipette tips.

Figure 7:
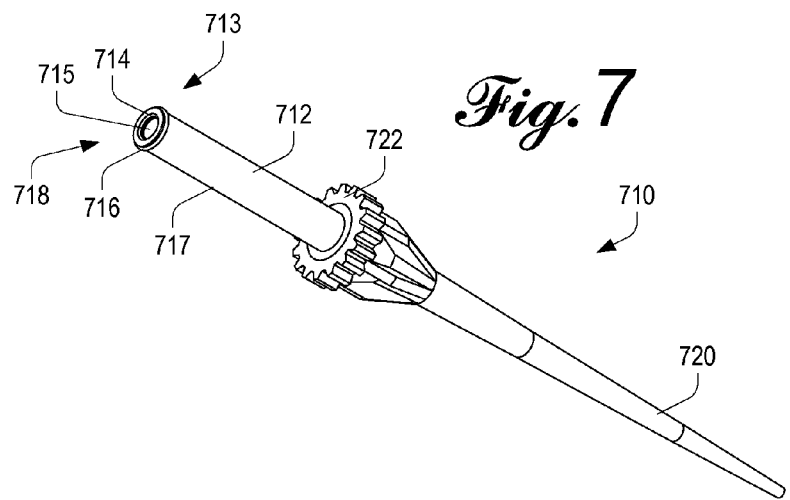
FIG. 7 illustrates an exemplary pipette tip according to the invention that accommodates approximately 20 μl of liquid, and emphasizes the proximal mount end of the pipette tip.

Another embodiment of a pipette tip according to the invention is illustrated in FIG. 7. The illustrated pipette tip 710 accommodates a liquid volume of approximately 20 µl in this configuration. As with the larger embodiment illustrated in FIGS. 2-6, a mount portion 712 of the pipette tip 710 extends into the shaft 112 of the pipette 110 and seals against the piston at its proximal end 713; the mount portion 712 will be described in further detail below in connection with FIGS. 9-11. As shown in FIG. 7, the mount portion 712 includes an annular sealing ring 714 around an interior surface 715 at the proximal end 713, and an annular mount projection 716 around an exterior surface 717 also at the proximal end 713. An open end 718 of the mount portion 712 receives the piston as described above and in further detail below.

Between the mount portion 712 and a liquid handling portion 720 of the pipette tip 710 is a peripheral shelf 722 that extends radially outward from the pipette tip. This peripheral shelf 722 may contact the distal end 120 of the pipette shaft 112 (FIG. 1) when the pipette tip 710 is mounted to the pipette 110 (but preferably does not, as described above), and serves as a surface for a pipette-mounted tip ejector 124 (FIG. 1) to act against. The peripheral shelf 722 may also limit the depth of insertion of the pipette tip 710 mount portion 712 into the shaft 112, and stabilize the pipette tip 710 against lateral forces exerted against the liquid handling portion 720 of the pipette tip 710.

Figure 8:
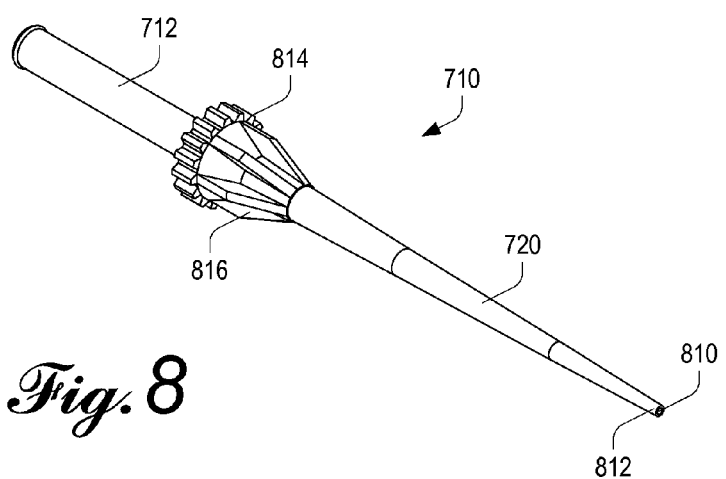
FIG. 8 presents an alternative view of the pipette tip of FIG. 7, emphasizing the distal liquid-handling end of the pipette tip.

Another view of the pipette tip 710 of FIG. 7 is presented in FIG. 8, illustrating an orifice 810 at a distal end 812 of the pipette tip 710. A plurality of radial fins 814 are arranged around an exterior of the pipette tip 710; these fins 814 provide a relatively wide surface to rest against an upper surface in a pipette rack, and further provide texture for ease in gripping and maneuvering pipette tips by hand. There may also be an aesthetic or trade-dress component to the configuration of the fins 814 on the pipette tip 710. In the disclosed embodiment, the fins 814 extend outward radially from the peripheral shelf 722 on the pipette tip 710, though other configurations are possible.

The embodiment illustrated in FIG. 8 further includes a set of bracing features 816 below the fins 814 and extending along the liquid handling portion 720 toward its distal end. The bracing features 816 reinforce the pipette tip 710 against undesired bending, and are configured to fit within the holes in a pipette tip rack. It will be noted that the 20 µl capacity tip 710 illustrated in FIGS. 7-8 is considerably narrower than the 200 µl capacity tip 210 illustrated in FIGS. 2-3, so the bracing features 816 are particularly desirable in this configuration. However, bracing or stiffening may be accomplished in other ways, or the bracing features 816 may be omitted entirely.

Figure 9:
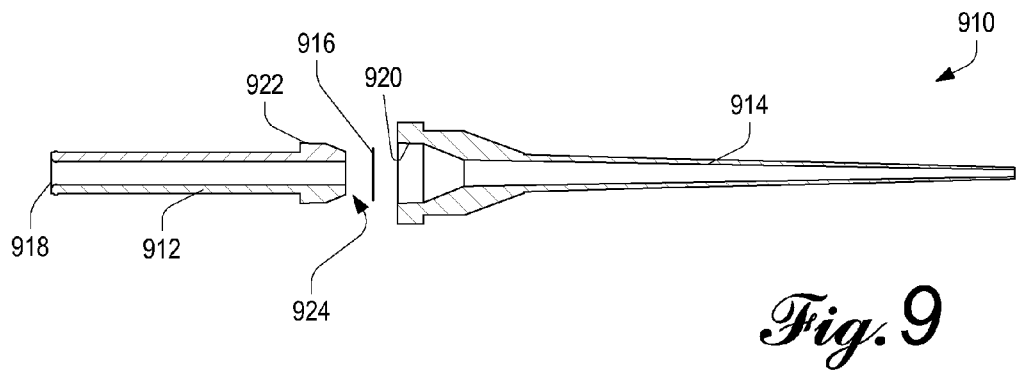
FIG. 9 is an exploded sectional view of the parts present in the pipette tip illustrated in FIG. 7.
Figure 10:
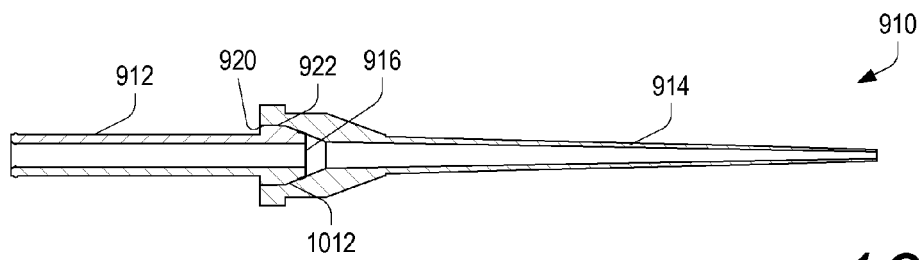
FIG. 10 is a sectional view of the pipette tip illustrated in FIG. 7, demonstrating the fit among the parts shown in FIG. 9.
Figure 11:
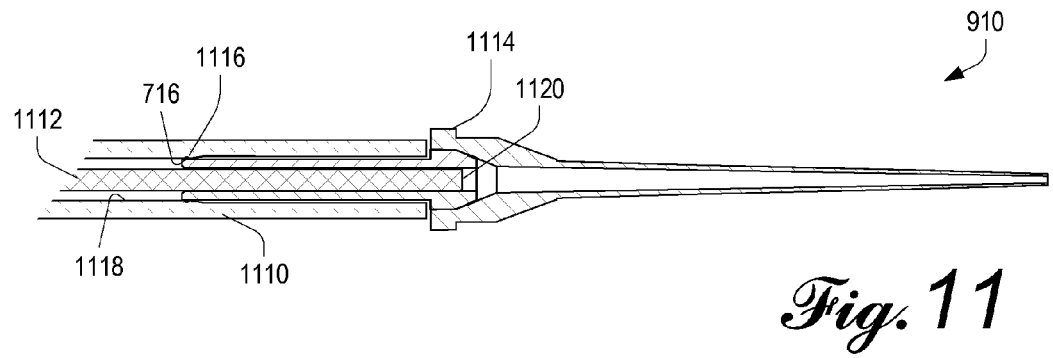
FIG. 11 is a sectional view of the tip illustrated in FIG. 7, showing the pipette tip mounted on a pipette shaft and sealing against a piston.

FIGS. 9, 10, and 11 illustrate the sealing pipette tip 710 of FIGS. 7-8 in cutaway form, viewed along a plane extending along the longitudinal axis of the tip 710 (FIG. 7).

One embodiment of a sealing pipette tip 710 according to the invention includes three constituent parts, and is illustrated in an exploded view in FIG. 9.

The pipette tip 910 of FIG. 9 includes a proximal mount segment 912, a tapered distal liquid handling segment 914, and a membrane filter 916. The parts are held together with an air-tight interference fit, preferably without adhesive. A connection end 918 of the proximal mount segment 912 attaches to a pipette according to the invention. Like the embodiment of FIGS. 2-6, the membrane filter is low pore size expanded PTFE. The membrane filter 916 is an optional component of a sealing tip 910 according to the invention, and if protection of the pipette's piston is not necessary or advantageous, it may be omitted. Alternative forms of filters, such as porous plastic plugs, may also be employed in a tip according to the invention. As with the embodiment illustrated in FIGS. 2-6, the constituent parts may be attached together by alternative means, other than the press fit shown in FIGS. 9-11.

As with the embodiment described in detail above, the disclosed sealing pipette tip 910 shown in FIGS. 7-11, being assembled from separate components, may advantageously employ separate materials for the mount segment 912 and the liquid handling segment 914.

FIG. 10 shows a sealing pipette tip 910 according to the invention in assembled form. As shown in FIG. 10, a relatively tight friction fit between an interior surface 920 of the liquid handling segment 914 and an exterior surface 922 of the mount segment 912 is sufficient to hold the parts together, to maintain an air-tight seal between the mount segment 912 and the liquid handling segment 914, and to maintain a desired position of the membrane filter 916 between the mount segment 912 and the liquid handling segment 914. As disclosed, the membrane filter 916 is sized slightly larger than the outer diameter of a cylindrical end 924 of the mount segment 912, and when the parts are pressed together, the membrane filter 916 bends around the flat cylindrical end 924 of the mount segment 912 and is held securely in place within the liquid handling segment 914.

It is recognized that the embodiment illustrated in FIGS. 7-11 includes a frustoconical interface 1012 between the mount segment 912 and the liquid handling segment 914, which is unlike the substantially cylindrical interface used in the embodiment illustrated in FIGS. 2-6. Any desirable contour for the interface between the mount segment and the liquid handling segment may be employed in a sealing pipette tip according to the invention, as long as the components are capable of being secured together for use, by press-fitting or any other means (such as adhesives or ultrasonic welding, if preferred). In an embodiment of the invention, interlocking features may be molded onto the mount segment and the liquid handling segment to enable a snap fit between the two pieces.

FIG. 11 shows the assembled sealing pipette tip 910 of FIG. 10 mounted on a portion of pipette shaft 1110, and further illustrating a pipette piston 1112 within the sealing tip 910.

As illustrated, a peripheral shelf 1114 abuts (or is closely adjacent to) a distal end of the pipette shaft 1110, the mount segment 912 of the sealing tip extends into an interior of the pipette shaft 1110. The piston 1112 extends within the mount segment 912 of the sealing tip 910.

The sealing tip 910 couples to the shaft 1110 by way of the mount projection 716 (FIG. 7), which engages a corresponding and mating mount recess 1116 extending around an interior surface 1118 of the shaft 1110. This engagement causes the sealing tip 910 to remain securely mounted on the pipette shaft 1110, even as the piston 1112 slides longitudinally within the sealing tip 910, contacting and sealing against the sealing ring 714 (FIG. 7).

With the pipette 110 set to its maximum volume setting, when the piston 1110 is in the released and extended position (and little or no pressure is exerted on the plunger button 116), a distal face 1120 of the piston 1110 only slightly penetrates the mount segment 912 of the pipette tip 910, a distance sufficient for the piston 1110 to engage the sealing ring 714 and form an air-tight seal, and preferably little further. As the plunger button 116 is depressed, the piston 1110 moves into the interior of the mount segment 912, displacing air within the pipette tip 910. And at the lowest point of the plunger button 116 corresponding to a completed blowout stroke, the distal face 1120 of the piston 1110 may be almost directly adjacent to the filter membrane 916, as illustrated in FIG. 11. Accordingly, the size of the space within the mount portion 912 of the pipette tip 910 is at least (and usually exceeds by as little as possible) the maximum liquid volume of the pipette tip 910 plus enough additional volume for the blowout stroke.

It should be noted that although the embodiment of the sealing tip 910 illustrated in FIGS. 9-11 is assembled from several parts, an alternative form may be manufactured as a single part, by injection molding or another suitable technique. Where the tip itself is fabricated in this manner, a traditional porous plastic filter may be inserted, as in commercially available traditional pipette tips.

Figure 12:
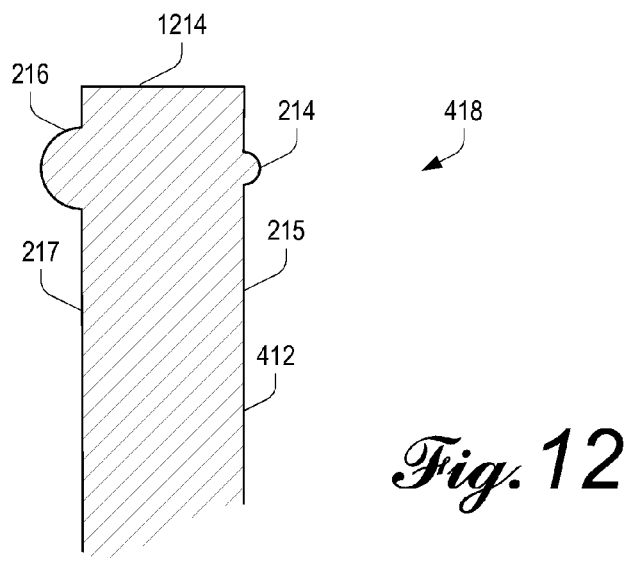
FIG. 12 is an enlarged cutaway view of a portion of the proximal mount end of a pipette tip according to the invention, such as the pipette tip illustrated in FIG. 2.

The connection end 418 of the proximal mount segment 412 of a pipette tip 410 (FIG. 4) according to the invention is illustrated in FIG. 12. A cross-section of the mount segment 412 (FIG. 4) is illustrated, including the mount projection 216 and seal ring 214 at the connection end 418 of the pipette tip 410.

The mount projection 216, as illustrated, has a semicircular cross-section that projects in an annular fashion around the exterior surface 217 of the mount segment 412 near the connection end 418. As will be illustrated in connection with FIG. 13 below, the mount projection 216 is configured to interlock with a corresponding feature on an interior surface of the pipette shaft. It should be noted that the semicircular cross-section is exemplary and only one possible configuration for the mount projection 216. Other shapes and configurations are possible, and a mass-produced pipette tip according to the invention is likely to have a mount projection that is deformed from the depicted symmetric shape simply as a result of routine design considerations, mold and process variations, ejecting the flexible material from its mold, and shrinkage during cooling.

Similarly, the illustrated sealing ring 214 has a semicircular cross-section projecting in an annular fashion around the interior surface 215 of the mount segment 412. The sealing ring 214 is configured to press against and form a seal with the piston. As with the mount projection 216, the sealing ring 214 has a semicircular cross-section for purposes of illustration only, and that shape represents only one possible configuration for the sealing ring 214. Other shapes and configurations are possible, and a mass-produced pipette tip according to the invention is likely to have a sealing ring 214 that is deformed from the depicted symmetric shape simply as a result of design considerations and the realities of injection molding as described above.

An embodiment of a connection end according to the invention might also define a bevel between its proximal surface and the interior surface of the mount segment. Such an optional bevel would tend to guide and to center the mount segment of the sealing pipette tip as the tip is mounted onto the shaft of the pipette 110, and to prevent the proximal surface of the mount segment from abutting against the piston 612 (FIG. 6) and resisting an attempt to mount the tip.

As disclosed, the mount projection 216 forms a substantially continuous annular ring around the entire periphery of the mount segment 412 of the pipette tip. It will be recognized, however, that the advantages of the invention may be realized by providing only small and separated bump-shape mount projections. For example, as few as three bumps evenly spaced around the mount segment 412 may provide adequate stability and mount security. Other configurations, both continuous and discontinuous, may be used.

Although certain characteristics of the mount segment 412 have been described in detail and illustrated in FIG. 12, it should be recognized that other aspects of the design may be altered without departing from the scope of the present invention. To provide two simple examples, the wall thickness of the mount segment 412 need not be substantially consistent as shown, and there may be a chamfer between the proximal surface 1214 and the mount projection 216; neither of these changes would cause the performance of a tip according to the invention to substantially depart from what is described herein. The illustrations set forth herein are intended to be schematic, and do not necessarily describe all functional and non-functional design details of a tip according to the invention.

Figure 13:
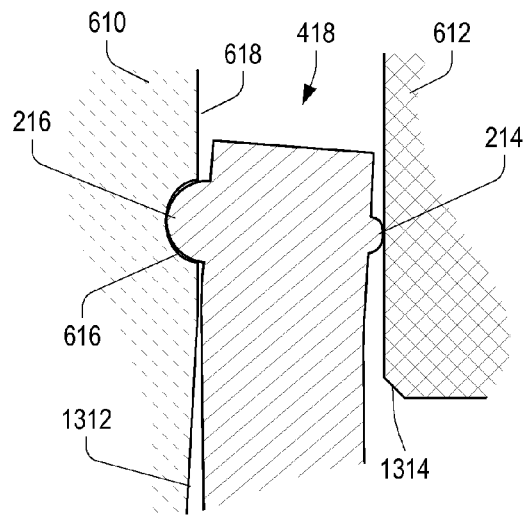
FIG. 13 is an enlarged cutaway view of a portion of the proximal mount end of a pipette tip according to the invention, such as the pipette tip illustrated in FIG. 2, showing the pipette tip mounted on a pipette shaft and sealing against a piston.

The connection end 418 of the proximal mount segment 412 of a pipette tip 410 (FIG. 6) according to the invention, along with corresponding portions of the pipette shaft 610 and piston 612, is illustrated in FIG. 13.

As described above in connection with FIG. 12, the mount projection 216 on the pipette tip interlocks with a mount recess 616 extending around an interior surface 618 of the pipette shaft 610. It will further be noted that as shown, at least a portion 1312 of the interior surface 618 of the shaft 610 is angled somewhat from a cylindrical configuration, forming a generally frustoconical interior surface that widens approaching the distal end 120 of the shaft 112 (FIG. 1).

Consequently, when the tip 410 is initially placed on the shaft 610 for mounting, there is little or no resistance, as the interior surface 618 of the shaft 610 (and the widening portion 1312) may be larger in diameter than the mount segment 412 including the mount projection 216, and the piston 612 is not yet within the sealing ring 214. As the tip 410 slides onto the shaft 610 and the peripheral shelf 222 (FIG. 2) approaches the distal end 120 of the shaft 112, the interior surface 618 progressively narrows, pushing inward on the connection end 418 of the mount segment 412, until the mount projection 216 reaches the corresponding mount recess 616 and interlocks. Meanwhile, the seal ring 214 is also compressed as the shaft 610 urges the connection end 418 of the mount segment 412 toward the piston 612. In the disclosed embodiment, the seal ring 214 has an uncompressed inner diameter approximately equal to or slightly larger than an outer diameter of the piston 612, and as the connection end 418 of the mount segment 412 is deformed by the narrowing interior surface 618 of the shaft 610, the seal ring 214 begins to contact the piston 612 and form an air-tight seal.

In an alternative embodiment of the invention, the tip 410 is configured so that the seal ring 214 of the mount segment 412 has a slightly smaller diameter than that of the piston 612. In this embodiment, the mounted tip 410 may seal against the piston 612 without the need for any additional force applied to the tip (such as through the mount projection 216), and the interior of the shaft 610 need not have a tapered profile.

The interlock between the mount projection 216 and the corresponding mount recess 616 on the shaft 610 ensures that the tip 410 remains substantially stationary as the piston 612 moves into and out of the tip 410, ensuring a generally linear relationship between the axial position of the piston 612 and the amount of air displaced by the piston 612 within the tip 410. For accurate performance, axial movement between the tip 410 and the shaft 610 should be avoided as the pipette 110 is operated.

As shown in FIG. 13, when the tip 410 is fully mounted on the pipette 110, the mount projection 216 is interlocked with the mount recess 616, and the seal ring 214 is pressed against the piston 612 to form a seal between the tip 410 and the piston 612. As illustrated, in this fully mounted position, the mount segment 412 may be somewhat deformed from its natural shape, pressed inward at the connection end 418 via the mount recess 616 and interior surface 618 of the shaft. The seal ring 214 is forced against the piston 612 sufficiently to deform the seal ring 214 slightly and ensure an effective air-tight seal, but not so much as to substantially restrict the axial movement of the piston 612 as directed by the user through the plunger button 116 and rod 118. Consequently, the mount segment 412 is made in a design and fabricated from a material that allows for reasonably unimpeded low-friction movement of the piston 612, even with the seal ring 214 pressed and deformed against the piston 612.

In an embodiment of the invention, the mount projection 216 has a radius that is equal to or slightly larger than the radius of the mount recess 616, to essentially immobilize the tip 410 when it is mounted on the pipette 110 by eliminating any substantial play between the mount projection 216 and the mount recess 616 (although other features of the shaft 610 and the tip 410 may also, or alternatively, be used to immobilize the tip on the shaft). Accordingly, the drawings of the parts set forth in FIG. 13 (and elsewhere) are intended to be schematic and to show general relationships, and may not be to scale.

As the piston 612 moves axially within the shaft 610 and the tip 410, the air displaced by the piston in the operation of the pipette 110 is entirely within the tip 410, and not necessarily within any other region of the pipette 110 or its shaft 610. Accordingly, there is no need for any seal between the piston 612 and any other portion of the pipette 110.

As shown in FIG. 13, the piston 612 includes a chamfer 1314 near its distal end, facilitating mounting the tip 410 on the shaft 610 by preventing the connection end 418 of the mount segment 412 from catching on the piston 612 and resisting insertion.

Figure 14:
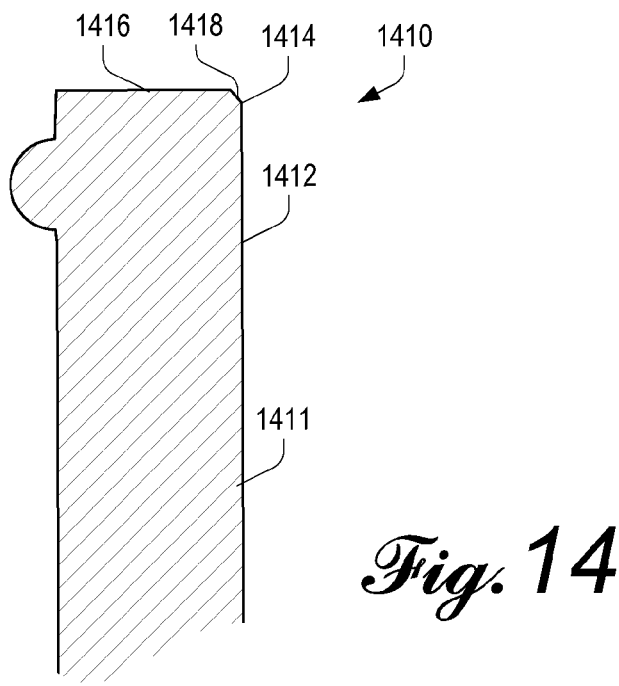
FIG. 14 is an enlarged cutaway view of a portion of the proximal mount end of an alternate embodiment of a pipette tip according to the invention, wherein the illustrated tip seals against a piston at a tip transition.
Figure 15:
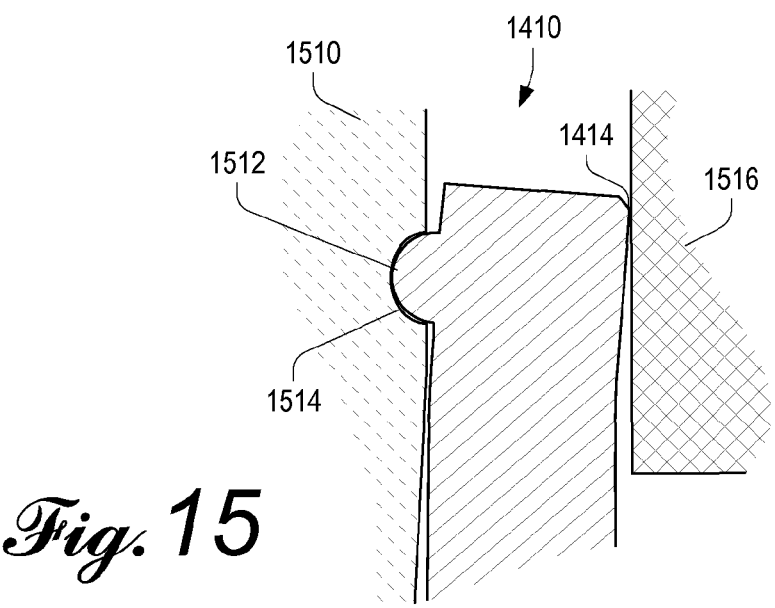
FIG. 15 is an enlarged cutaway view of a portion of the proximal mount end of the pipette tip according to the invention of FIG. 14, showing the pipette tip mounted on a pipette shaft and sealing against a piston.

FIGS. 14 and 15 illustrate an alternate form of a connection end 1410 on a mount segment 1411 of a tip according to the invention. The connection end 1410 illustrated in FIG. 14 has no sealing ring protruding from its interior surface 1412, and is intended to seal against the piston of a pipette according to the invention at a location 1414 on a chamfer 1418 transitioning between the interior surface 1412 and a proximal surface 1416.

As shown in FIG. 15, when mounted on a pipette shaft 1510, once again the mount projection 1512 is interlocked with the mount recess 1514, and the connection end 1410 of the mount segment 1411 is deformed to press the sealing location 1414 against the piston 1516, thereby creating a substantially air tight seal.

Alternatively, this form of transition seal may also be employed in a tip that omits the chamfer 1418, in which case the seal between the piston 1516 and the connection end 1410 of the tip would occur in an annulus defining the transition between the interior surface 1412 and the proximal surface 1416.

Figure 16:
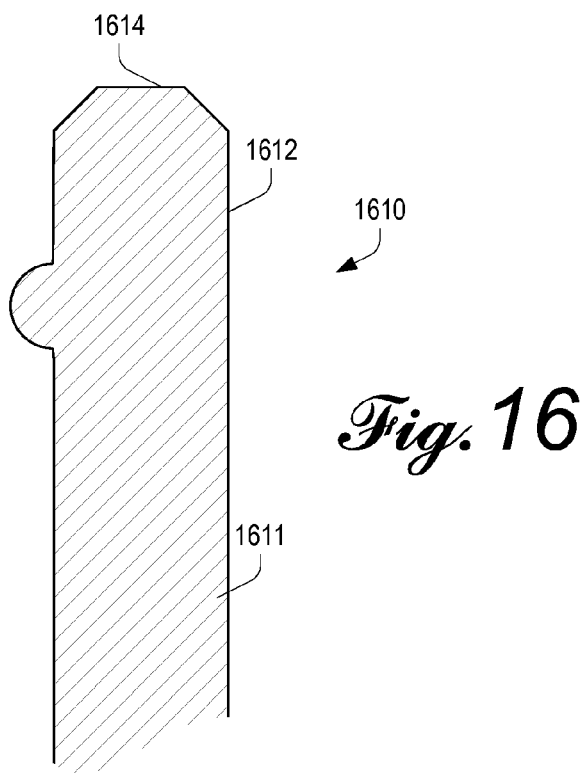
FIG. 16 is an enlarged cutaway view of a portion of the proximal mount end of an alternate embodiment of a pipette tip according to the invention, wherein the illustrated tip seals against a piston along an internal surface.
Figure 17:
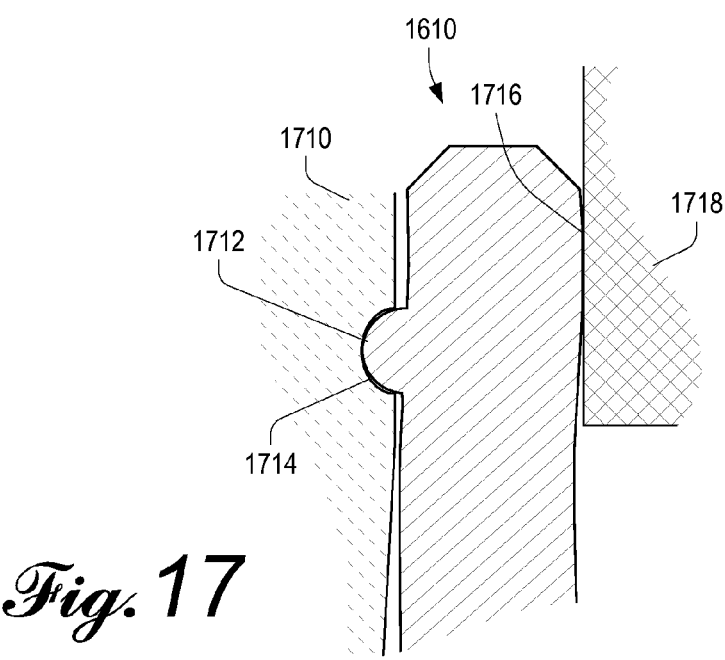
FIG. 17 is an enlarged cutaway view of a portion of the proximal mount end of the pipette tip according to the invention of FIG. 16, showing the pipette tip mounted on a pipette shaft and sealing against a piston.

FIGS. 16 and 17 illustrate another alternate form of a connection end 1610 on a mount segment 1611 of a tip according to the invention. In the connection end 1610 illustrated in FIG. 16, no sealing ring protrudes from the interior surface 1612; rather, an annular region of the interior surface 1612, near a proximal end 1614 of the mount segment 1611, is intended to seal against the piston.

As shown in FIG. 17, when mounted on a pipette shaft 1710, once again the mount projection 1712 is interlocked with the mount recess 1714, and the connection end 1610 of the mount segment 1611 is deformed inwardly to press the annular seal region 1716 against the piston 1718, thereby creating a substantially air tight seal.

Although the embodiments illustrated in FIGS. 12-17 seal differently against the piston 612, 1516, or 1718, they are all shown with a mount projection 216, 1512, or 1712 that cooperates with a mount recess 616, 1514, or 1714 on an interior surface of the shaft 610, 1510, or 1710 to mount the tip 114 to a pipette 110 according to the invention. Additional alternatives are possible, including mount projections that are not necessarily opposite or axially proximate to the seal ring.

Figure 18:
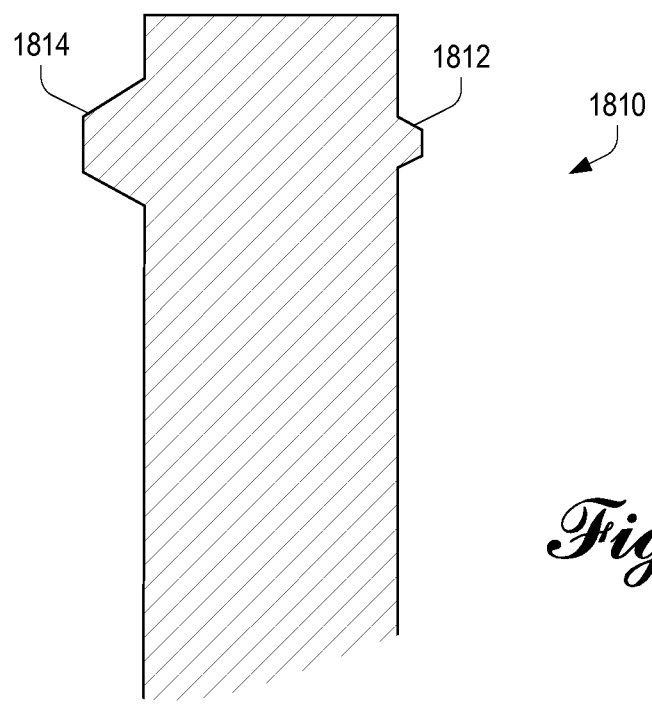
FIG. 18 illustrates an alternate embodiment of the mount and seal structures of FIG. 12.

It will be noted that the contours of the mount projection 216 and the seal ring 214 (FIG. 12) are depicted herein as largely smooth, with a generally semi-circular cross section. It will be noted that a proximal mount segment 1810 according to the invention may have a different profile. As shown in FIG. 18, the mount segment 1810 has a seal ring 1812 and a mount projection 1814, each with a cross section defined by relatively straight line segments. A tip having the profile illustrated in FIG. 18 is substantially functionally equivalent to a tip having the profile illustrated in FIG. 12. Of course, other configurations are possible and within the discretion of a skilled mold designer, and are deemed to be within the scope of the present invention even if strict functional equivalency is not maintained. As a practical matter, it should be observed that even if an injection mold adheres to certain desired dimensions and profiles, the actual shapes of the parts ejected from the mold may differ quite dramatically, as a result of cooling, shrinkage, ejection from the mold, other handling steps, and additional factors not described herein. Tips having these altered characteristics may be quite deformed from a desired shape, the profiles illustrated herein, or the shape of the mold, but are nonetheless also considered within the scope of the present invention.

The pipette 110 illustrated in FIG. 1 includes an ejector button 128 coupled to the ejector 124 external to the pipette shaft 112, as is common in traditional handheld pipettes. Generally, with such a configuration, a pipette tip is ejected from the pipette by applying pressure to the ejector button 128 to act against spring resistance, causing the ejector button 128 to depress and move axially toward the distal end 120 of the pipette 110. This force is transferred through a mechanism in the pipette 110 to the ejector 124, which acts against the tip 114, pushing it off the distal end 120 of the shaft 112.

With a seal-less pipette and sealing tip according to the invention, however, it is possible to relocate the ejector to a location inside the shaft. A pipette with an internal ejection mechanism may be easier to clean than traditional external-ejection pipettes, and the ejection mechanism may be made more resistant to breakage caused by external forces or impacts. Moreover, the pipette may be made smaller, permitting access to smaller areas, as the shaft need not have external parts for tip ejection. It may further be aesthetically preferable to have a smooth pipette shaft with no visible ejection mechanism.

Figure 19:
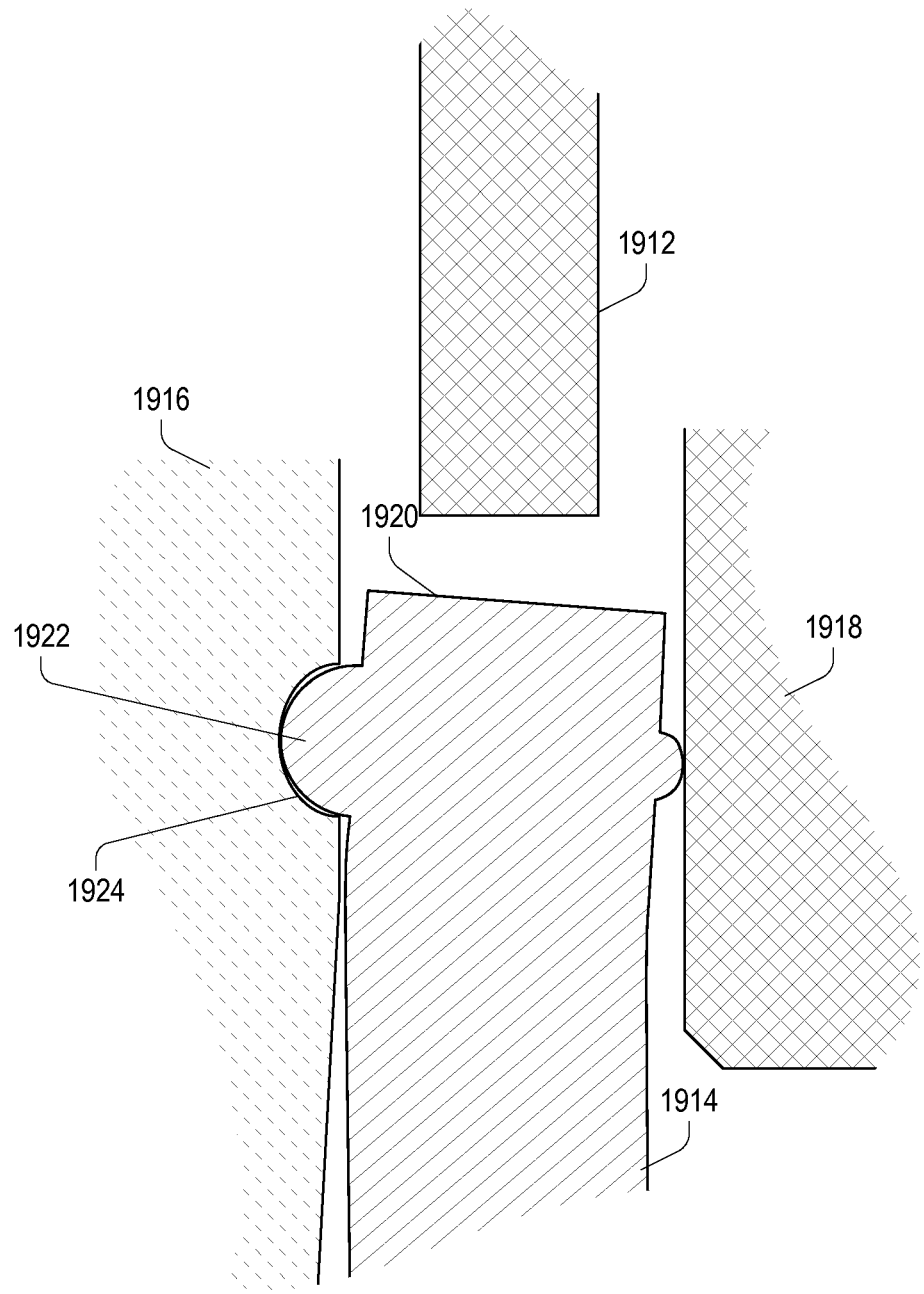
FIG. 19 illustrates a version of the pipette shaft, piston, and tip illustrated in FIG. 13, with the pipette including an internal tip ejector according to the invention.

An embodiment of this configuration, with an internal ejector 1912, is illustrated in FIG. 19. In the illustrated embodiment, the mount segment 1914 of the tip 114 couples to the shaft 1916 and seals against the piston 1918 as in other embodiments (e.g., the version illustrated in FIG. 13), but in the space between the shaft 1916 and the piston 1918, the internal ejector 1912 is mounted for axial movement. In its unactuated position, the rod 1912 is positioned to avoid or barely touch the proximal surface 1920 of the mount segment 1914 of the pipette tip 114 mounted to the shaft 1916. Accordingly, the internal ejector 1912 does not interfere with mounting the tip. When pressure is applied to the ejector button 128 (FIG. 1), the ejector 1912 is caused to move axially and act against the proximal surface 1920 of the pipette tip, dislodging the mount projection 1922 from the mount recess 1924, and pushing the tip 114 off the shaft 1916.

In the described embodiment, the internal ejector 1912 is coupled to the ejector button 128, as described above, generally through a mechanical linkage. But alternatively, the internal ejector 1912 may be actuated through a linkage to the piston 1918 or the plunger button 116 mechanism (FIG. 1), taking effect and acting against a mounted tip 114 only when the plunger button is passed through and beyond the blowout position, at which point all liquid has been discharged from the tip. In an embodiment of the invention, the ejector 1912 comprises a step or other projection on the piston of the pipette 110, contacting and acting against the tip 114 only when the plunger button is depressed past blowout as described above.

When internal ejection is used as described herein and illustrated in FIG. 19, it should be noted that the peripheral shelf 222 (FIG. 2) need not extend radially out beyond the edge of the pipette shaft 112 (FIG. 1); such a shelf need not exist at all. With a traditional ejection mechanism, the peripheral shelf 222 may provide a surface against which the external ejector 124 may act, but this function is not required when an internal ejector 1812 acts against a portion of the tip 114 internal to the shaft 112.

It should be noted that the ejector 1912 need not take the form of a physical rod, as that term is generally understood to be an elongated cylinder or prism. Rather, the internal ejector 1912 may be generally annular at its distal end, where it contacts and acts against the also annular proximal surface 1920 of the tip 114. Other shapes and configurations are possible and are considered to be within the scope of the invention.

In summary, then, because a pipette tip 114 according to the invention seals directly against the piston 612, a pipette according to the invention need not include any internal sealing mechanism, thereby eliminating an internal pipette seal as a potential point of failure, and reducing the need for regular pipette service. A pipette 110 according to the invention may have a configuration generally comparable to traditional and other commercially available pipettes, but lacking the internal seal, and with a shaft 112 configured to mount a pipette tip 114 described herein.

Figure 20:
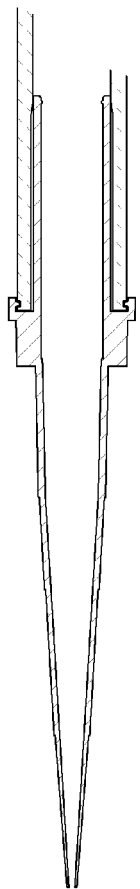
FIG. 20 illustrates an alternate embodiment of the shaft and tip of FIG. 6, in which the tip locks to the shaft via an external groove defined by the shaft and a projection near a peripheral shelf of the tip.
Figure 21:
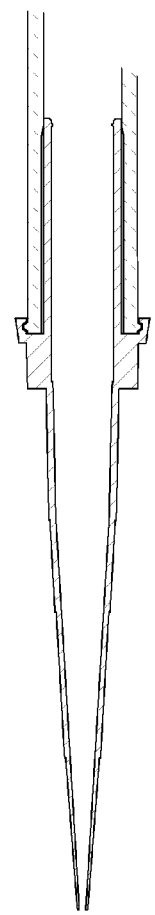
FIG. 21 illustrates an alternate embodiment of the shaft and tip of FIG. 6, in which the tip locks to the shaft via an external projection on the shaft and a recess defined by a peripheral shelf of the tip.

It should also be noted that other means of attaching the tip 114 to the shaft 112 are possible. For example, an interlocking mechanism may be provided external to the shaft 112. In alternative embodiments a projection or clips on or around the peripheral shelf 222 (FIG. 2) of a tip according to the invention may cooperate with corresponding features (such as a groove) on an outer surface of the shaft. One example of such a configuration is shown in FIG. 20. Alternatively, a projection on the shaft may interlock with one or more recesses on the tip. One such version of this alternative is shown in FIG. 21. These alternative embodiments and others are deemed to be within the scope of the current invention. As with other drawings herein, FIGS. 20-21 may have exaggerated feature shapes and sizes to emphasize the general functional configuration, and hence should be regarded as schematic.

Figure 22:
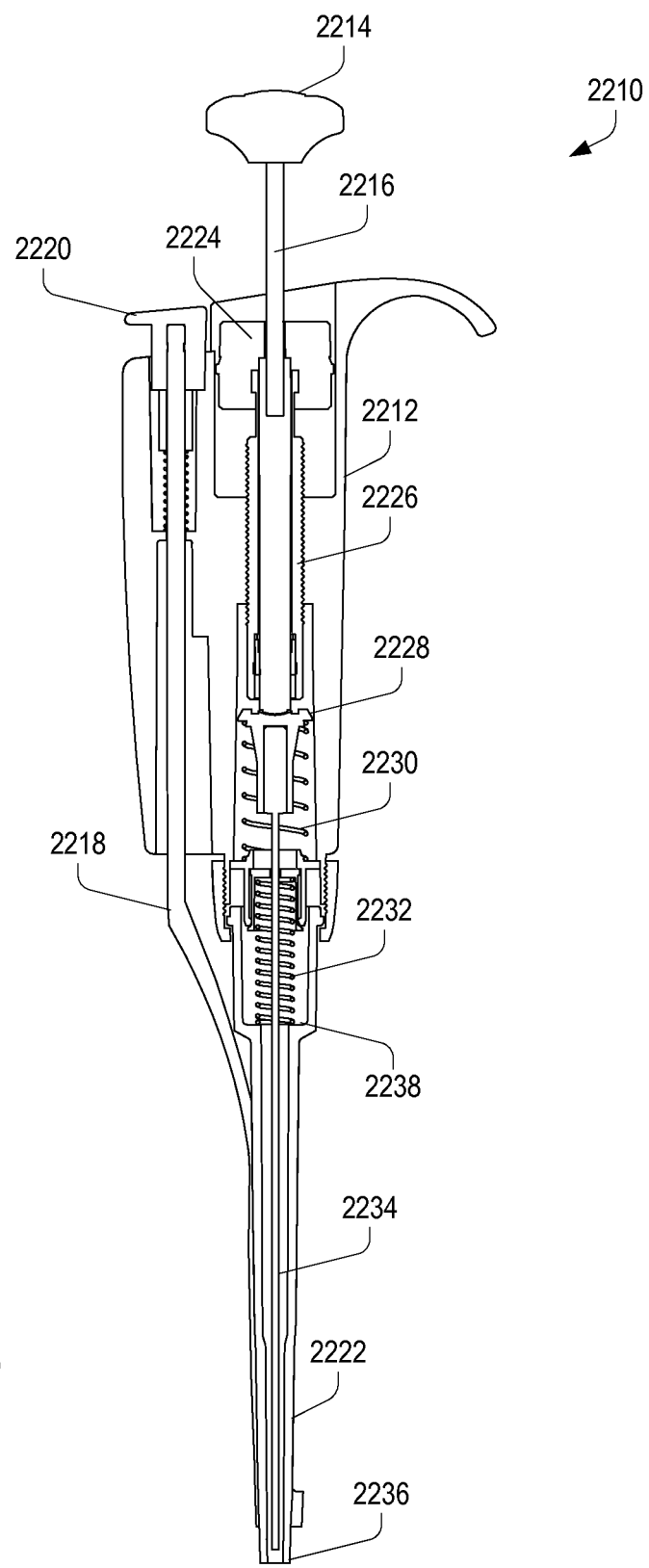
FIG. 22 illustrates one possible embodiment of a seal-less pipette according to the invention.

One embodiment of a seal-less pipette 2210 according to the invention is illustrated in FIG. 22. The illustrated embodiment is a simplified representation of the RAININ CLASSIC pipette available from Rainin Instrument, LLC, modified for use with the sealing pipette tips described herein.

Like the embodiment illustrated in FIG. 1, it includes a hand-holdable body 2212, a plunger button 2214 and a plunger rod 2216 used to operate the pipette 2210, a tip ejector 2218 coupled to an ejector button 2220, and a tip-mounting shaft 2222.

Internally, the structure is in some ways similar to a comparable traditional pipette. The volume setting mechanism, including a volume knob 2224 and a volume-setting screw 2226 may be adapted from a traditional pipette. The plunger rod 2216 acts against a piston assembly 2228, which is spring-biased upward by a stroke spring 2230 and a blowout spring 2232, the latter of which is compressed only as the piston assembly 2228 crosses a specified home position.

It will be noted, however, that the piston assembly 2228 includes an elongated piston 2234 extending axially through the shaft 2222; this elongated piston 2234 seals against a tip according to the invention that is mounted to a distal end 2236 of the shaft 2222 as described and illustrated elsewhere herein.

In a traditional pipette, the piston would be sealed against the shaft, typically by means of an o-ring or other annular seal; in the RAININ CLASSIC pipette, such a seal is placed between the blowout spring and an internal step in the shaft 2222, such as the step 2238 shown in FIG. 22.

It will be observed that no seal is present in the embodiment illustrated in FIG. 22, in the region around the step 2238 in the shaft 2222, corresponding to where a seal would be placed in a traditional pipette having a similar form factor. Nor is there required to be a seal between the piston 2234 and any other part of the pipette 2210. Although the pipette 2210 may include structure for ensuring centering or alignment of the piston 2234 within the shaft 2222, and such structure may at times tend to impede airflow within the pipette 2210 or around the piston 2234, there is no need for an air-tight seal in a pipette according to the invention.

It should be observed that while the foregoing detailed description of various embodiments of the present invention is set forth in some detail, the invention is not limited to those details and a sealing pipette tip and seal-less pipette made according to the invention can differ from the disclosed embodiments in numerous ways. In particular, it will be appreciated that embodiments of the present invention may be employed in many different fluid-handling applications. It should be noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An air displacement pipette comprising:
   an elongated tip-mounting shaft having a distal end and an interior surface;
   a piston mounted for axial movement within the shaft, wherein an interior space is defined around the piston by the interior surface of the shaft; and
   a pipette tip having a generally elongated tubular configuration and comprising a mount portion including an open proximal end and an inward-facing sealing region, and a liquid handling portion including a tapered open distal end, the mount portion of the pipette tip being adapted for sliding insertion into the distal end of the shaft;
   wherein, when the pipette tip is mounted on the shaft, the mount portion of the pipette tip extends into the interior space between the piston and the interior surface of the shaft, the piston penetrates the open proximal end of the pipette tip and is axially movable within the mount portion of the tip, the sealing region of the pipette tip forms an air tight seal against the piston, and an air volume is maintained between a distal face of the piston and any liquid in the pipette tip and displaced by axial movement of the piston.

2. The air displacement pipette of claim 1, wherein the sealing region comprises a projecting sealing ring.

3. The air displacement pipette of claim 2, wherein the sealing ring has a diameter smaller than the diameter of the piston when the tip is not mounted on the shaft.

4. The air displacement pipette of claim 2, wherein the sealing ring has an uncompressed diameter approximately equal to or larger than the diameter of the piston when the tip is not mounted on the shaft.

5. The air displacement pipette of claim 4, wherein the sealing ring is compressed against the piston by the mounting shaft when the tip is mounted on the pipette.

6. The air displacement pipette of claim 1, further comprising cooperative structures on the pipette shaft and pipette tip for limiting the axial travel of the tip on the shaft to insure uniform depth of mounting shaft penetration into the pipette tip.

7. The air displacement pipette of claim 6, wherein the cooperative structures comprise at least one recess on one of a surface of the shaft and the pipette tip, and at least one corresponding projection on the other of the surface of the shaft and the pipette tip, and wherein the recess and projection mutually interlock and prevent the tip from moving axially with respect to the pipette when the piston is moved through the air tight seal.

8. The air displacement pipette of claim 1, further comprising a tip ejector adapted to slidably eject the pipette tip from the shaft by selectively applying an axial force to the pipette tip to push it off the distal end of the shaft.

9. The air displacement pipette of claim 5, wherein the pipette further comprises a tip ejector adapted to slidably eject the pipette tip from the shaft by selectively applying an axial force to the pipette tip to push it off the distal end of the shaft, and wherein the pipette tip is free to drop off the shaft when the seal ring is no longer compressed against the piston.

* * * * *